(12) United States Patent
Kobayashi et al.

(10) Patent No.: US 10,285,420 B2
(45) Date of Patent: May 14, 2019

(54) MAGNETITE-BASED HETEROGENEOUS ICE-CRYSTAL NUCLEATION

(71) Applicant: CALIFORNIA INSTITUTE OF TECHNOLOGY, Pasadena, CA (US)

(72) Inventors: Atsuko Kobayashi, Tokyo (JP); Joseph L. Kirschvink, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 3 days.

(21) Appl. No.: 15/406,603

(22) Filed: Jan. 13, 2017

(65) Prior Publication Data
US 2017/0119028 A1    May 4, 2017

Related U.S. Application Data

(60) Continuation-in-part of application No. 15/131,657, filed on Apr. 18, 2016, now abandoned, which is a
(Continued)

(51) Int. Cl.
| | |
|---|---|
| *A23L 3/36* | (2006.01) |
| *A23B 7/04* | (2006.01) |
| *H01F 1/03* | (2006.01) |
| *F25B 19/00* | (2006.01) |
| *F25B 21/00* | (2006.01) |

(Continued)

(52) U.S. Cl.
CPC .............. *A23L 3/36* (2013.01); *A01N 1/0278* (2013.01); *A01N 1/0294* (2013.01); *A23B 7/04* (2013.01); *A23L 3/32* (2013.01); *A23L 3/363* (2013.01); *F25B 19/005* (2013.01); *F25B 21/00* (2013.01); *H01F 1/0306* (2013.01); *H01F 1/0313* (2013.01); *A23V 2002/00* (2013.01); *F25B 2321/002* (2013.01)

(58) Field of Classification Search
CPC ................................ A23L 3/36; A01N 1/0278
See application file for complete search history.

(56) References Cited

U.S. PATENT DOCUMENTS

| | | |
|---|---|---|
| 1,835,557 A | 12/1931 | Burke et al. |
| 6,250,087 B1 | 6/2001 | Owada et al. |
| | (Continued) | |

FOREIGN PATENT DOCUMENTS

| | | |
|---|---|---|
| JP | S529970 A | 1/1977 |
| JP | 2001-086967 A | 4/2001 |
| | (Continued) | |

OTHER PUBLICATIONS

Kirschvink et al., "Magnetite in human tissues: a mechanism for the biological effects of weak ELF magnetic fields," Bioelectromagnetics Supplement 1:101-113, 1992.*
(Continued)

*Primary Examiner* — Rosanne Kosson
(74) *Attorney, Agent, or Firm* — Steinfl + Bruno, LLP (57) ABSTRACT

Ice nucleation and supercooling are controlled by the presence of magnetite particles. Magnetite decreases supercooling and promotes ice nucleation. Therefore, freezing of liquid solutions occurs at higher temperature compared to supercooled solutions. Applying a magnetic field allows control of supercooling and ice nucleation.

5 Claims, 3 Drawing Sheets

Related U.S. Application Data division of application No. 14/328,602, filed on Jul. 10, 2014, now Pat. No. 9,339,027.

(60) Provisional application No. 62/278,048, filed on Jan. 13, 2016, provisional application No. 61/859,940, filed on Jul. 30, 2013.

(51) Int. Cl.
  *A01N 1/02* (2006.01)
  *A23L 3/32* (2006.01)

(56) References Cited

U.S. PATENT DOCUMENTS

| | | |
|---|---|---|
| 7,237,400 B2 | 7/2007 | Owada et al. |
| 7,810,340 B2 | 10/2010 | Owada et al. |
| 2009/0199577 A1 | 8/2009 | Owada et al. |
| 2015/0037782 A1 | 2/2015 | Kobayashi et al. |
| 2016/0227763 A1 | 8/2016 | Kobayashi et al. |

FOREIGN PATENT DOCUMENTS

| | | |
|---|---|---|
| JP | 2004081133 A | 3/2004 |
| WO | 0124647 A1 | 4/2001 |

OTHER PUBLICATIONS

Japanese Patent Office Official Action for Japanese Patent Application No. 2016-531762. dated May 29, 2018. 17 pages. (Japanese Original + English Translation).
Abedini, S., et al., "Effects of cryopreservation with a newly-developed magnetic field programmed freezer on periodontal ligament cells and pulp tissues", *Cryobiology*, 62 (2011) 181-187.
Adair, R.K. "Constraints on biological effects of weak extremely-low-frequency electromagnetic fields",*Phys. Rev. A.*, 43 (2) (1991) 1039-1048.
Allen, P.H.G. "Electric stress and heat transfer", *British Journal of Applied Physics*, 10 (1959) 347-351.
Bonjour,E., et al., "Electroconvection effects on heat transfer",*Chem. Eng. Prog.*, 58 (7) (1962) 63-66.
Brem, F., et al "Magnetic iron compounds in the human brain: a comparison of tumour and hippocampal tissue", *Journal of the Royal Society Interface*, 3 (2006) 833-841.
Choi, H.Y. "Electrohydrodynamic condensation heat transfer", *Journal of Heat Transfer*,90 (1968) 98-102.
Cobine, J.D. "Ch. 19—Other Electrostatic Effects and Applications" in: A.D. Moore, (Ed.), *Electrostatics and Its Applications*, Wiley, New York, (1973) 441-455.
Collingwood, J.F., et al., "Three-dimensional tomographic Imaging and characterization of iron compounds within Alzheimer's plaque core material", *Journal of Alzheimer's Disease*, 14 (2008) 235-245.
Dobson, J., et al, "Magnetic properties of human hippocampal tissue—evaluation of artefact and contamination sources", *Brain Research Bulletin*; 39 (4) (1996) 255-259.
Dunn, J.R., et al. "Magnetic material in the Human hippocampus", *Brain Research Bulletin*36 (2) (1995) 149-153.
Eder, S.H.K., et al., "Magnetic characterization of isolated candidate vertebrate magnetoreceptor cells", *Proceedings of the National Academy of Sciences of the United States of America*, 109 (30) (2012) 12022-12027.
Final Office Action for U.S. Appl. No. 15/131,657, filed Apr. 13, 2016 on behalf of California Institute of Technology. dated Jan. 5, 2017. 8 pages.
Gould, J.L., et al., "Bees have magnetic remanence", *Science*, 201 (4360) (1978) 1026-1028.
Grassi-Schultheiss, P.P., et al., "Analysis of magnetic material in the human heart, spleen and liver", *BioMetals*, 10 (1997) 351-355.
Gunders, D. "Wasted: How America is Losing Up to 40 Percent of Its Food from Farm to Fork to Landfill", *NRDC Issue Paper Natural Resources Defense Council*, (2012) 26 pages.

Hautot, D., et al., "Preliminary observation of elevated levels of nanocrystalline iron oxide in the basal ganglia of neuroferritinopathy patients", *Biochimica Et Biophysica Acta*, 1772 (2007) 21-25.
Hautot, D., et al., "Superconducting quantum interference device measurements of dilute magnetic materials in biological samples",*Review of Scientific Instruments*, 76 (2005) 045101-1 to 045101-4.
International Search Report for International Application No. PCT/US2014/047884 filed Jul. 23, 2014 on behalf of California Institute of Technology. dated Nov. 11, 2014. 6 pages.
Kaku, M., et al., "Cryopreservation of periodontal ligament cells with magnetic field for tooth banking", *Cryobiology*, 61 (2010) 73-78.
Kaku, M., et al., "Electric and magnetic fields in cryopreservation: A response", *Cryobiology*, 64 (2012), 304-305.
Kirschvink, J.L., et al., "Biogenic magnetite as a basis for magnetic field detection in animals", *BioSystems*, 13 (1981) 181-201.
Kirschvink, J.L., et al,, "Comment on 'Constraints on biological effects of weak extremely-low-frequency electromagnetic fields'", *Physical Rev. A.*, 46 (4) (1992) 2178-2184.
Kirschvink, J.L., et al., "Magnetite biomineralization in the human brain", *Proceedings of the National Academy of Sciences*, 89 (1992) 7683-7687.
Kirschvink, J.L., et al., "Magnetite-based Magnetoreception", *Current Opinion in Neurobiology*, 11 (2001) 462-467.
Kirschvink, J.L. "Rock Magnetism linked to Human Brain Magnetite", *EOS, Trans. Am. Geophysical Union*, 75 (15) (1994) 178-179.
Kirschvink-Kobayashi, A., et al., "Electrostatic enhancement of industrial drying processes", *Ind. Engin. Chem. Proc. Design & Develop.*, 25 (4) (1986) 1027-1030.
Kobayashi, A., et al, "Ch. 21—Magnetoreception and Electromagnetic Field Effects: Sensory Perception of the Geomagnetic Field in Animals & Humans" (in M. Blank, (Ed.), Electromagnetic Fields: Biological Interactions and Mechanisms, *American Chemical Society Books*, Washington, D.C.) (1995) 367-394.
Kobayashi, A., et al, "Experimental observation of magnetosome chain collapse in magnetotactic bacteria: Sedimentological, paleomagnetic, and evolutionary implications", *Earth and Planetary Science Letters*, 245 (2006) 538-550.
Kobayashi, A.K., et al., "Ferromagnetism and EMFs", *Nature*, 374 (1995) 123.
Kobayashi, A.K., et al., "Studies of inorganic crystalline solid in biosystem—magnetite in the Human Body", *J. Japanese Society of Powder and Powder Metallurgy*, 43 (11) (1996) 1354-1360.
Kobayashi, A.K., et al., "Studies of inorganic crystals in biological tissue: magnetite in human tumor", *J. Japanese Society of Powder and Powder Metallurgy*,44 (1997) 294-300.
Kronig, R., et al., "On the theory of heat transfer from a wire in an electric fieid",*Applied Scientific Research Section a—Mechanics Heat Chemical Engineering Mathematical Methods*, 1 (1947) 35-46.
Lee, S.Y., et al., "Magnetic Cryopreservation for Dental Pulp Stem Cells", *Cells Tissues Organs*, 196 (2012) 23-33.
Lin, P.Y., et al., "Cryopreservation of human embryonic stem cells by a programmed freezer with an oscillating magnetic field", *Cryobiology*, 66 (2013), 256-260.
Lowenstam, H.A., "Magnetite in denticle capping in recent chitons (polyplacophora)", *Geol. Soc. Am. Bull.*, 73 (1962) 435-438.
Lykoudis, P.S., et al., "The influence of electrostrictive forces in natural thermal convection", *International Journal of Heat and Mass Transfer* 6(1963) 853-862.
Moore, E.B., et al., "Structural transformation in supercooled water controls the crystallization rate of ice", *Nature*, 479 (2011) 506-508.
Naito, M., et al., "Effect of a Magnetic Field on *Drosophila* under Supercooled Conditions", *Plos One*7 (2012) 5 pages.
Non-Final Office Action for U.S. Appl. No. 15/131,657, filed Apr. 13, 2016 on behalf of California Institute of Technology. dated Oct. 19, 2016. 8 pages.
Pankhurst, Q., et al., "Increased levels of magnetic iron compounds in Alzheimer's Disease", *Journal of Alzheimer's Disease*, 13 (2008) 49-52.

(56) References Cited

OTHER PUBLICATIONS

Restriction Requirement for U.S. Appl. No. 14/328,602, filed Jul. 10, 2014 on behalf of California Institute of Technology. dated Aug. 5, 2015. 10 pages.
Robinson, M., "Convective heat transfer at the surface of corona electrode", *International Journal of Heat and Mass Transfer*, 13 (1970) 263-274.
Non-Final Office Action for U.S. Appl. No. 14/328,602, filed Jul. 10, 2014 on behalf of California Institute of Technology. dated Oct. 28, 2015. 8 pages.
Notice of Allowance for U.S. Appl. No. 14/328,602, filed Jul. 10, 2014 on behalf of California Institute of Technology. dated Jan. 21, 2016. 10 pages.
Suzuki, et al., T., "Experimental Investigation of Effectiveness of Magnetic Field on Food Freezing Process." *Transactions of the Japan Society of Refrigerating and Air Conditioning Engineers*, 26 (4) (2009) 371-386. English Summary.
Walcott, C., et al., "Pigeons have magnets", *Science*, 205 (1979) 1027-1029.
Walker, M.M., et al., "A candidate magnetic sense organ in the Yellowfin Tuna *Thunnus albacares*", *Science*, 224 (1984) 751-753.
Walker, M.M., et al., "Ch. 20—Magnetoreception and Biomineralization of Magnetite Fish" (in J.L. Kirschvink, et al., Magnetite Biomineralization and Magnetiteoreception in Organisms: A New Biomagnetism, Plenum Press, New York, N.Y.), 1985, 417-437.
Walker, M.M., et al., "Ch. 5—Detection, Extraction, and Characterization of Biogenic Magnetite" (in J.L. Kirschvink, et al., *Magnetite Biomineralization and Magnetoreception in Organisms: A New Biomagnetism*, Plenum Press, New York, N.Y.) (1985) 155-166.
Walker, M.M., et al., "Production of single-domain magnetite throughout life by sockeye salmon, Oncorhynchus nerka", *J. Exptl. Biol.*,140 (1988) 51-63.
Wowk, B., "Electric and magnetic fields in cryopreservation", *Cryobiology*, 64 (2012), 301-303.
Written Opinion for International Application No. PCT/US2014/047884 filed Jul. 23, 2014 on behalf of California Institute of Technology. dated Nov. 11, 2014. 6 pages.
Atkinson et al. "The importance of feldspar for ice nucleation by mineral dust in mixed-phase clouds" *Nature, Macmillan Publishers Ltd*. Jun. 2013. vol. 498. pp. 355-358, 490. 5 pages.
Butler et al. "Theoretical Single-Domain Grain Size Range in Magnetite and Titanomagnetite" *Journal of Geophysical Research, American Geophysical Union*. Oct. 1975. vol. 80, No. 29, pp. 4049-4058. 10 pages.
Butler, R. F. "Paleomagnetism: Magnetic Domains to Geologic Terranes" *Blackwell Scientific Publications*. 1992. 248 pages. (Book).
Cisowski, S. "Interacting vs. non-interacting single-domain behavior in natural and synthetic samples" *Physics of the Earth and Planetary Interiors, Elsevier*. 1981. vol. 26. pp. 56-62. 7 pages.
Cochet et al. "Ice crystallization by *pseudomonas syringae*" *Applied Microbiology and Biotechnology, Springer-Verlag*. 2000. vol. 54. pp. 153-161. 9 pages.
Dahl et al. "High-pressure freezing for the preservation of biological structure—Theory and Practice" *Journal of Electron Microscopy Technique, Alan R. Liss*. 1989. vol. 13. pp. 165-174. 11 pages.
Diaz Ricci et al. "Magnetic Domain State and Coercivity predictions for Biogenic Greigite (Fe3S4): A Comparison of Theory with Magnetosome Observation" *Journal of Geophysical Research, American Geophysical Union*. Nov. 1992. vol. 97, No. B12. pp. 17309-17315. 7 pages.
Feinberg et al. "Effects of internal mineral structures on the magnetic remanence of silicate-hosted titanomagnetite inclusions: an electron holography study" *Journal of Geophysical Research, American Geophysical Union*. 2006. vol. 111. pp. 1-11. 11 pages.
Feinberg et al. "Exsolved magnetite inclusions in silicates: features determining their remanence behavior" *GEOLOGY, Geological Society of America*. 2005. vol. 33, No. 6. pp. 513-516. 4 pages.

Frankel et al. "Magnetite in Freshwater Magnetotactic Bacteria" *SCIENCE, American Association for the Advancement of Science*. Mar. 1979. vol. 203, No. 30, pp. 1355-1356. 3 pages.
Gajdardziska-Josifovska et al. "Discovery of nanocrystalline botanical magnetite" *European Journal of Mineral, E. Schweizerbart'sche Verlagsbuchhandlung*. 2000. vol. 13. pp. 863-870. 8 pages.
Holland et al. "Bats use magnetite to detect the Earth's magnetic field" *PLoS One, Public Library of Science*. Feb. 2008. vol. 3. No. 2. 4 pages.
John Morris et al. "Controlled ice nucleation in cryopreservation" *Cryobiology, Elsevier*. 2013. vol. 66. pp. 85-92. 10 pages.
Kirschvink et al. "Mineralization and Magnetization of Chiton Teeth: Paleomagnetic, Sedimentologic, and Biologic Implications of Organic Magnetite" *Earth and Planetary Science Letters, Elsevier*. 1979. vol. 44. pp. 193-204. 12 pages.
Kirschvink et al. "Rapid, precise, and high-sensitivity acquisition of paleomagnetic and rock-magnetic data: Development of a low-noise automatic sample changing system for superconducting rock magnetometers" *G3—Geochemistry, Geophysics, Geosystems, American Geophysical Union*. May 2008. vol. 9, No. 5. pp. 1-18, 18 pages.
Kobayashi et al. "A ferromagnetic model for the action of electric and magnetic fields in cryopreservation" *Cryobiology, Elsevier*. 2013. vol. 68. pp. 163-165. 3 pages.
Kobayashi et al. "Ferromagnetism and EMFs" *Nature, Nature Publishing Group*. Mar. 1995. vol. 374. pp. 123. 1 page.
Le Sage et al. "Optical magnetic imaging of living cells" *Nature, Nature Publishing Group*. Apr. 2013. vol. 496. pp. 486-489. 15 pages.
Lowenstam, H. A. "Minerals made by organisms" *SCIENCE, American Association for the Advancement of Science*. Mar. 1981. vol. 211, No. 13. pp. 1126-1131. 7 pages.
Malkin et al. "Stacking disorder in ice I" *Physical Chemistry Chemical Physics, Royal Society of Chemistry*. 2015. vol. 17. pp. 60-76. 17 pages.
Mann et al. "Ultrastructure, Morphology and Organization of Biogenic Magnetite from Sockeye Salmon, Oncorhynchus Nerka: Implications for Magnetoreception" *The Journal of Experimental Biology, The Company of Biologists Ltd*. 1988. vol. 140. pp. 35-49. 16 pages.
Mazur et al. "Cryopreservation of the Germplasm of Animals Used in Biological and Medical Research: Importance, Impact, Status, and Future Directions" *Biology of Reproduction, Society for the Study of Reproduction*. 2007. vol. 78, No. 1. pp. 2-12. 12 pages.
Munro et al. "Evidence for a Magnetite-Based Navigational "Map" in Birds" *Naturwissenschaften, Springer-Verlag*. 1997. vol. 84. pp. 26-28. 3 pages.
Saville, D.J. "Multiple comparison procedures—the practical solution" *The American Statistician, American Statistical Association*. 1990. vol. 44, No. 2. pp. 174-180.
Shaw et al. "Heterogeneous Surface Crystallization observed in Undercooled Water" *Journal of Physical Chemistry B—Letters, American Chemical Society*. 2005. vol. 109. pp. 9865-9868. 4 pages.
Japanese Patent Office Official Action for Japanese Patent Application No. 2016-531762. dated Jan. 8, 2019. 11 pages (Japanese Original + English).
Tarduno et al. "Geomagnetic field strength 3.2 billion years ago recorded by single silicate crystals" *Nature, Nature Publishing Group*. Apr. 2007. vol. 446, No. 5. pp. 657-660. 4 pages.
Tarduno et al. "High geomagnetic intensity during the midcretaceous from Thellier analyses of single plagioclase crystals" *SCIENCE, American Association for the Advancement of Science*. Mar. 2001. vol. 291. pp. 1779-1783. 6 pages.
Weiss et al. "Magnetic microscopy promises a leap in sensitivity and resolution" *Eos, American Geophysical Union*. Oct. 2001. vol. 82, No. 44.
Whale et al. "A technique for quantifying heterogenous ice nucleation in microlitre supercooled water droplets" *Atmospheric Measurement Techniques, Copernicus Publications*. 2015. vol. 8. pp. 2437-2447. 12 pages.
Wiltschko et al. "A magnetic pulse leads to a temporary deflection in the orientation of migratory birds" *Experientia, Birkauser Verlag*. 1994, vol. 50. pp. 697-700. 7 pages.

(56) References Cited

OTHER PUBLICATIONS

Zhang et al. "Impact of Surface Nanostructure on Ice Nucleation" *Journal of Chemical Physics, American Institute of Physics.* 2014. vol. 141, pp. 124709-1-124709-7. 8 pages.

\* cited by examiner

MAGNETITE-BASED HETEROGENEOUS ICE-CRYSTAL NUCLEATION

CROSS REFERENCE TO RELATED APPLICATIONS

The present application is a Continuation-In-Part of U.S. application Ser. No. 15/131,657 filed on Apr. 18, 2016 which, in turn, is a Divisional of U.S. application Ser. No. 14/328,602 filed on Jul. 10, 2014 which, in turn, claims priority to U.S. Provisional Application No. 61/859,940 filed on Jul. 30, 2013. The present application also claims priority to U.S. Provisional Application No. 62/278,048, filed on Jan. 13, 2016. The disclosures of all of the above applications are incorporated herein by reference in their entirety.

TECHNICAL FIELD

The present disclosure relates to ice-crystal nucleation. More particularly, it relates to magnetite-based heterogeneous ice-crystal nucleation in cryopreservation and other processes.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, a method is described, the method comprising: controlling ice nucleation and supercooling in a liquid solution, the liquid solution comprising magnetite particles, by applying said liquid solution.

In a second aspect of the disclosure, a method is described, the method comprising: controlling heat input and output within a freezing-based temperature control system with a liquid solution of magnetite particles.

In a third aspect of the disclosure, a method is described, the method comprising: controlling ice nucleation and supercooling in clouds by injecting magnetite particles into the clouds.

DETAILED DESCRIPTION

An outstanding biophysical puzzle is focused on the apparent ability of weak, extremely low-frequency oscillating magnetic fields to enhance cryopreservation of many biological tissues. A recent theory holds that these weak magnetic fields could be inhibiting ice-crystal nucleation on the nanocrystals of magnetite ($Fe_3O_4$, an inverse cubic spinel) that are present in many plant and animal tissues and often formed through natural biochemical processes, by causing them to oscillate. In this theory, magnetically-induced mechanical oscillations disrupt the ability of water molecules to nucleate on the surface of the magnetite nanocrystals. However, the ability of the magnetite crystal lattice to serve as a template for heterogeneous ice crystal nucleation is as yet unknown, particularly for particles in the 10-100 nm size range. The present disclosure describes how the addition of trace amounts of finely-dispersed magnetite into ultrapure water samples strongly reduces the incidence of supercooling, as measured in experiments conducted using a controlled freezing apparatus with multiple thermocouples. SQUID (superconducting quantum interference device) magnetometry was used to quantify nanogram levels of magnetite in the water samples. The present disclosure also describes the relationship between the volume change of ice, and the degree of supercooling, that may indicate decreased degassing during the crystallization of supercooled water. In addition to supporting the role of ice-crystal nucleation by biogenic magnetite in many tissues, magnetite nano-crystals could provide inexpensive, non-toxic, and non-pathogenic ice nucleating agents needed in a variety of industrial processes, as well as influencing the dynamics of ice crystal nucleation in many natural environments.

An ability to freeze biological tissues without causing ultra-structural damage has been a concern of the Electron Microscopy (EM) community for many years. Extensive work by transmission and scanning (TEM/SEM) electron microscopists has shown that freezing rates of ~10,000° C./s are needed to prevent cellular damage, and this can only be achieved for very thin tissue layers at atmospheric pressure. Using high-pressure techniques that move a sample at room temperature into the ice-stability field, followed by cooling, still only allows a tissue thickness of up to 0.6 mm to be processed.

Conversion of a liquid to a solid during freezing requires structural ordering at the molecular level, which is often inhibited unless seed nuclei or epitaxial surfaces are present to help initiate the crystallization process. Retention of the liquid state at temperatures below the melting point is called supercooling, and is a dynamically unstable state in many liquids due to the chance probability of an initial seed crystal nucleating. The rapid cooling techniques for thin samples, noted above, work by forcing the water to supercool faster than damaging ice crystals are able to nucleate. Supercooling is actually a general phenomenon: standardized tables of physical properties of various compounds will list the melting temperature of a substance, rather than its freezing temperature. Melting is the disruption of a pre-existing, ordered atomic lattice, which occurs when the thermal background energy is high enough to disrupt the atomic ordering of a crystal lattice; this happens at temperatures that are far more reproducible than the 'freezing' temperature.

Supercooling is easily achieved in purified bottled water that has been packaged in amorphous PET (polyethylene terephthalate) bottles, and makes for many impressive video demonstrations that are available online. Molecular dynamic studies of the crystallization of ice-$I_h$ (hexagonal ice polymorph I) suggest that upwards of 250-300 discrete water molecules need to assume a transient long-range ordering in the supercooled state in order to initiate crystal nucleation. Once this low-probability, stochastic nucleation is initiated anywhere in the container, it will spread rapidly until the large latent heat of crystallization of water (~80 calories/g) brings the bulk temperature of the crystallizing mush back up to the melting temperature (0° C.), producing a characteristic step function (105) in the time-temperature profile of supercooled water; an example is shown here in FIG. 1, panel a. Subsequent cooling has little additional effect on the temperature curve, until most of the liquid water that has buffered the material at the freezing point has been incorporated into the growing volume of ice. In contrast, water that contains particles capable of rapidly nucleating ice crystals will not show a pronounced supercooling effect, resulting in more conventional cooling curves like those shown in FIG. 1, panels b and c.

Figure 1:
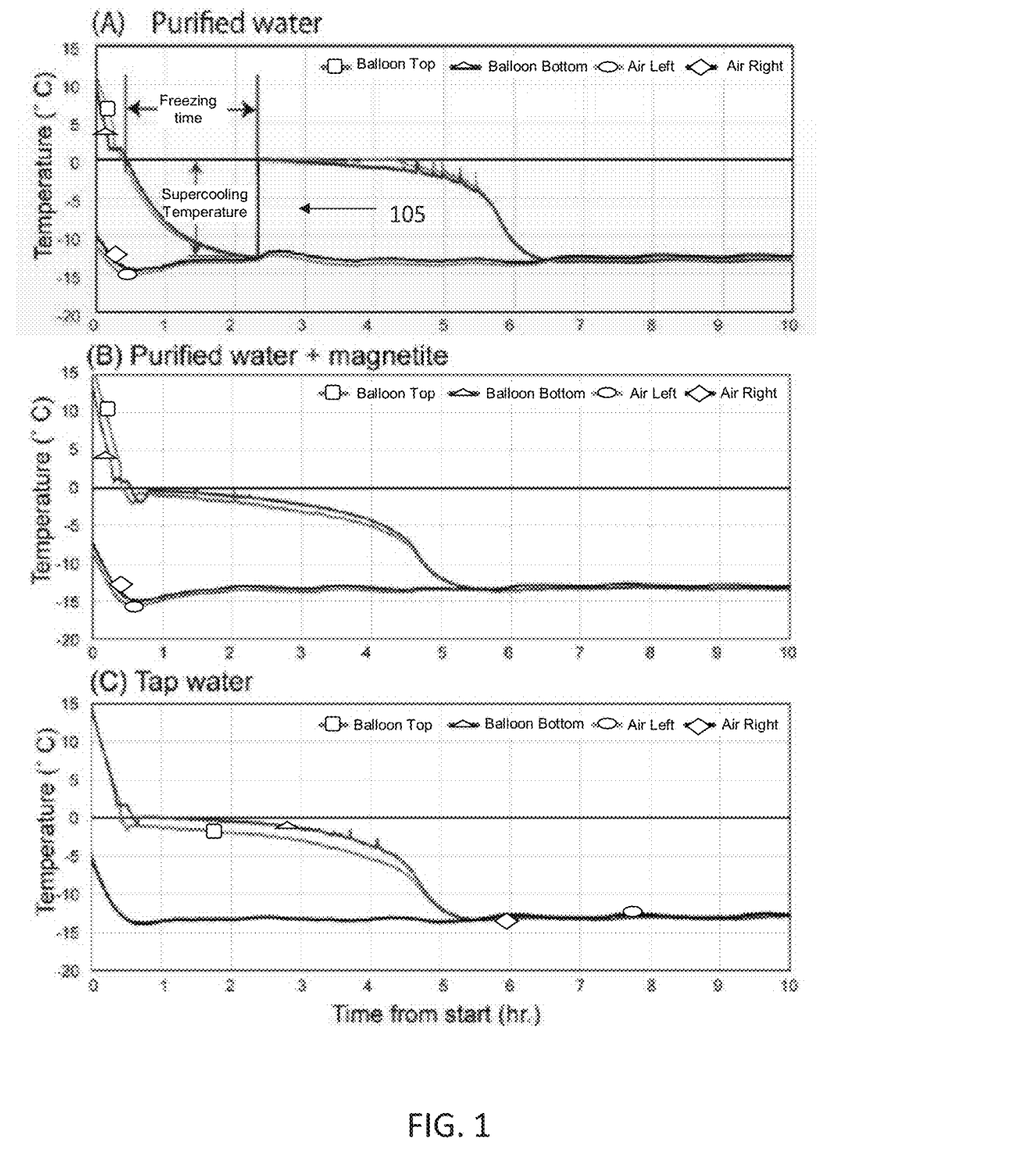
FIG. 1 illustrates examples of time-temperature curves.

FIG. 1 illustrates examples of time-temperature curves for standard balloon samples, as monitored by the thermocouples placed near the top and bottom of the balloons, and at two points in the cooling chamber: in panel a, typical example of purified water showing supercooling (Labels show how and where the freezing times and lowest supercooling temperatures were measured from the bottom sensor data, as entered in Table 1); in panel b, typical example of purified water spiked with ~70 ng/g of standard magnetite powder; in panel c, cooling curve of laboratory tap water.

In nature, ice crystals are thought to nucleate on small dust particles made of a variety of common mineral types that are distributed by aeolian and fluvial processes, and are present in most natural freshwater and marine bodies of water, as well as forming the dominant aerosol component in the atmosphere. Most of the research has been focused on common minerals found in aeolian dust, as well as condensed organic materials. On the other hand, Atkinson et al. (Ref. [1]) have found that the potassium-rich feldspars provide better ice nucleation sites than the other minerals. In any event, mineral dusts that serve as ice nucleation particles may play a significant role in the dynamics of atmospheric convection and radiation, particularly in view of the large latent heat of crystallization.

With these properties in mind, it is important to mention that ice damage to animal and plant membranes during intracellular freezing is a major obstacle to the use of cryopreservation. The damage is two-fold: the ~10% expansion as water freezes changes the relative volume ratio of membranes to cytosol, potentially disrupting the cytoskeleton and cellular membranes, and, if the crystallization process is slow, needle-like ice crystals can form that can puncture holes in cell membranes as they grow. However, it is a puzzle as to how such intracellular ice crystals actually nucleate, as most cellular materials are composed of long polymers (DNA, fatty acids, protein α-helices and β-sheets, tubes, etc.) which lack the highly regular ordering and surface area that are thought to play a role in the epitaxial organization of seed nuclei. In this respect, most cellular materials are more like the surface of PET bottles than crystals, although there is evidence suggesting that some organisms have evolved mechanisms to control this process. In higher animals and plants, most of the nutrients and water are absorbed at the molecular scale via transport processes through cell membranes after digestion; this process tends to exclude the mineral dusts that might be present in an organism's food and water supply.

An exception to this is the presence of occasional biomineral products in animal and plant tissues, which might serve as the ice nucleation sites that normally prevent supercooling. Lowenstam and Weiner (Ref [31]) reviewed ~60 discrete minerals products that organisms are known to make through biochemical processes, most of which have very specialized roles in the highly-localized formation of bones, teeth, spicules, otoliths, and shells. Lowenstam (Ref [30]) noted that biominerals range in a spectrum, from minerals that form as an extracellular byproduct 'induced' by biological activity, to highly controlled intracellular precipitates, mediated by specific organic matrices and vesicles. They also range in structural ordering from cryptocrystalline materials like the ball of iron oxide (ferrihydrite) at the core of the ferritin molecule, to the ordered arrays of aragonite needles in the nacre of molluscan shells. Very few of these highly crystalline biomineral products are present in tissues outside the heavily-mineralized areas.

In contrast, nanocrystals of biological magnetite ($Fe_3O_4$), and its topotactic solid-solution end-member, maghemite, ($\gamma$-$Fe_2O_3$), are broadly distributed at low concentration density throughout many animal tissues, and even in at least one group of plants. As referred to here, 'magnetite' is taken to refer to any crystal with a composition in the magnetite to maghemite solid-solution series. Magnetite biomineralization was first discovered in 1962 by Heinz Lowenstam in the teeth of the chitons (marine mollusks of the class Polyplacophora), where it hardens the major lateral teeth that the animals use for scraping endolithic algae off of rocky substrates. It was subsequently discovered in the magnetotactic bacteria, honeybees, homing pigeons, fish, and even grasses. Although experiments with pulse-remagnetization demonstrate that some of these particles are involved in the ability of animals to detect the geomagnetic field, only a few magnetite-containing cells in an animal would be needed for magnetoreception. Far too much is present in most animal tissues for that to be the only function.

Specialized studies in the field of rock magnetism using ultra-sensitive superconducting quantum-interference device magnetometers (SQUIDs) in clean-lab environments can detect picogram quantities of single-domain magnetite in gram-size tissue samples. Standard rock-magnetic techniques demonstrate that most of these particles are dispersed in isolated particles or small clumps, rather than in the concentrated aggregates like the chiton teeth. Typical concentrations of magnetite in animal tissues inferred from these studies range from 1 to 100 ng/g, with particle sizes in the 10-100 nm size range where they have been extracted and examined with high-resolution TEM.

It can be noted that if magnetite crystals in this size range can serve as ice crystal nucleation templates, concentrations as low as 1 ppb can still be significant, as a single 50 nm particle of magnetite in a 50 mm cubic cell occupies 1 ppb by volume. An ice crystal blade nucleating anywhere in a cell at the freezing point could grow large enough to freeze the cell, possibly rupturing the cell membrane. It can be noted that trace concentrations of biogenic magnetite are common in organic matter, potentially confounding the assumption that organic matter is amorphous.

It is therefore of fundamental importance for cryobiology and cryopreservation and for any process involving ice crystal formation to know whether or not nanocrystals of magnetite like those distributed through many animal and plant tissues are effective for heterogeneous ice crystal nucleation, and whether or not the supercooling process itself has a volumetric effect on the ice expansion process. Similarly, as magnetite is common in the environment, it could play an important role for controlling ice nucleation in nature. It might also serve as an effective ice-nucleating agent in industrial processes where supercooling needs to be inhibited. Hence, the present disclosure describes a series of controlled freezing experiments with well-characterized water samples, with and without added nanophase magnetite, aimed at testing both the nucleation hypothesis, and the concept that ice resulting from supercooled water might have different volume expansion characteristics. The results described herein support both hypotheses at very highly significant levels, and support the concept that oscillating magnetic fields jiggling ferromagnetic particles in biological samples can explain the reduction of tissue damage during freezing.

In order to produce a uniform environment for monitoring the freezing properties of our water samples, a large volume refrigerator that could be controlled accurately and stably in the 20° to 0° temperature range. Our initial measurements of commercial (home) freezers revealed that the cooling cycles were highly variable, particularly those that employed 'defrosting' techniques. Therefore, a standard −80° C. biological laboratory refrigerator was used.

Figure 2:
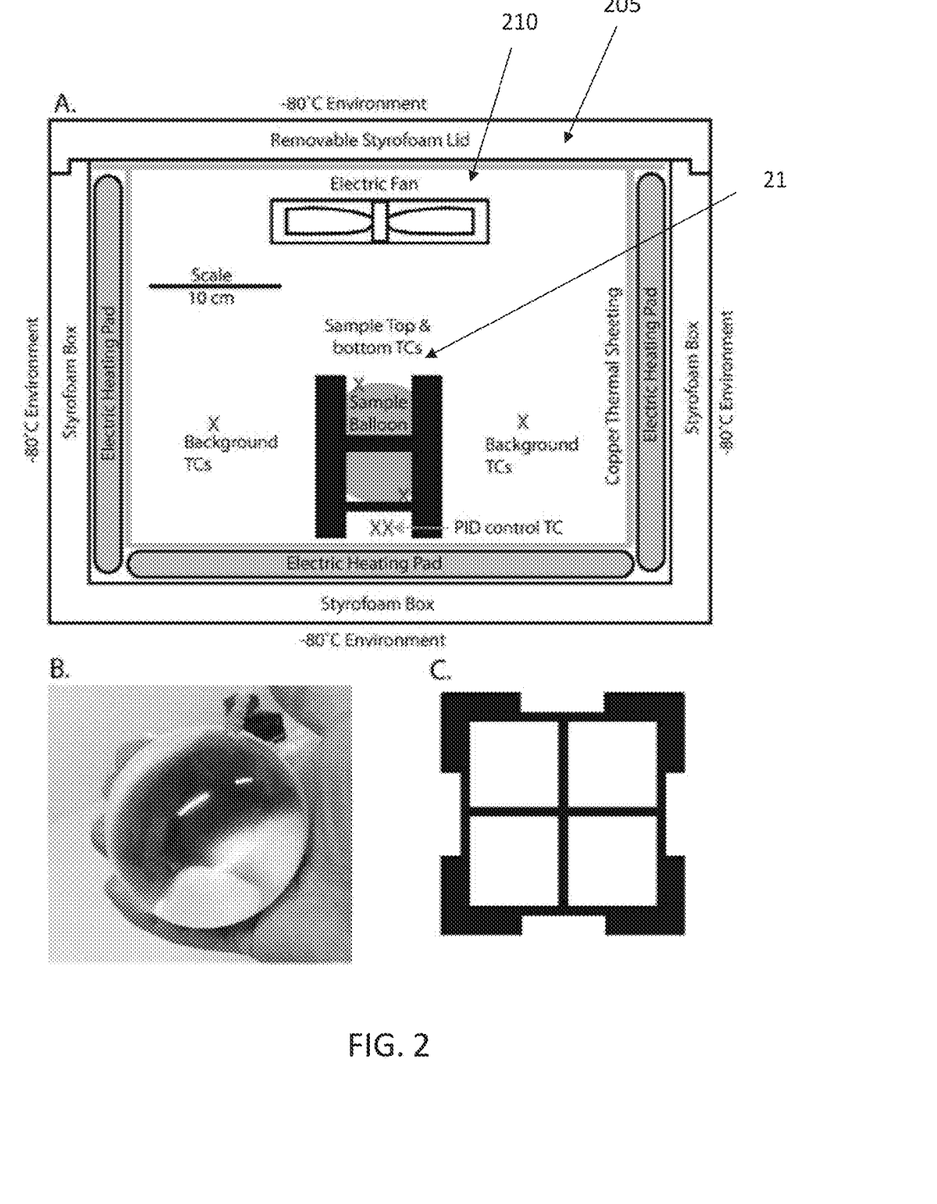
FIG. 2 illustrates a thermal monitoring device for standard balloon samples.

It was discovered that the cryogenic design is specifically engineered for the lowest value, with no options of intermediate control. For that reason a stable, adjustable-temperature chamber was created within this refrigerator, using a 50×37×38 cm Styrofoam™ box with 3 cm thick walls, as shown in FIG. 2. Five of the inside surfaces of the box (all but the top, which had to be removable) were covered with thermal heating pads controlled by an external, tunable proportional integral derivative (PID) controller. To reduce temperature variability within the chamber, a 0.3 mm thick copper foil was placed over the heating pads, and suspended a small fan on a removable platform over the top to prevent thermal stratification of the cold air in the chamber.

To minimize the variability in our experimental results, and to mimic the freezing of typical 100+ gram biological samples, standard balloons were made out of stretchable, ~0.1 mm thick polyurethane film, that could be cleaned in concentrated HCl to remove surface contaminants that are typically present on virtually all laboratory surfaces. Balloons were formed from pairs of 9 cm discs of the film, with 1.5 cm necks, heat-fused along the edges, including the neck. This design allows ~140 g of water without air bubbles to be inserted via an acid-cleaned, 200 ml syringe. (Particles at the air/water interface can sometimes increase ice crystal nucleation, so it is important to minimize air bubbles in the experimental balloons.) An example of this balloon is shown in FIG. 2, panel b.

FIG. 2 illustrates a thermal monitoring device for standard balloon samples: in panel a, side-view schematic diagram of the Styrofoam™ experimental freezing chamber, showing the approximate locations of the electric heating pads, the copper sheets, air circulation fan, and the plastic support frame for the balloon samples; in panel b, image of the custom-made polyurethane balloon, filled with water; in panel c, top-view of the plastic support frame for the standard balloons.

The ultrapure water samples were produced with an ion exchange/distillation unit. Comparisons reported below were made with the ultra-pure water that had been spiked with a well-characterized magnetite powder, as well as ordinary tap water.

To measure the volume change of these water-filled balloons before and after freezing, a glass flask was modified with a drip nozzle that allowed accurate collection of liquid equal in volume to that of an inserted object. First ethanol was poured, chilled to ~−15° C. to the glass nozzle, then a water-filled balloon was lowered into the container until the top surface was submerged. Then the volume of spilled ethanol was measured, which is the same as that of the balloon before freezing. After the experiment this measurement was repeated on the frozen balloon to measure its volume after freezing. The difference was subtracted, and the volume change was estimated, as shown in Table 1 and FIG. 3.

Water-filled balloons described above were inserted into a custom-built plastic support cube that allowed air to circulate freely. Two surface-mounted type "T" thermocouples were taped near the top and bottom of the spherical balloons, with a small quantity of petroleum jelly to ensure good thermal contact. Additional thermocouples were spaced around the freezing container to monitor the temperature within the system. A computing interface board that allows 8 thermocouples to be monitored simultaneously was used. Monitoring software was written in C#, using the device drivers provided for this language. Data were recorded in 1 or 2-s intervals, and saved in digital form during the course of all freezing experiments.

Synthetic magnetite powder was used, with a nominal particle size of 50-100 nm, which had been previously characterized by rock-magnetic properties, and EM. These particles are single magnetic domains that are stably and uniformly magnetized at the saturation value of 92 $Am^2/kg$. As these highly magnetic crystals will clump together into dense clusters, it is not easy to disperse them into a larger volume of water. Ultrasonic treatment, for example, actually causes particles to 'find' each other and clump together.

However, application of an oscillating magnetic field stronger than the microscopic coercivity of the particles can break up these clumps into small strings as the magnetic moments flip, occasionally yielding inter-particle repulsive forces that help to disperse them. Hence, several liters of magnetite-spiked water were prepared by first adding 0.25 ml of the magnetite powder to 0.5 ml of ultrapure water, and then exposing it to a 100 mT, 50 Hz alternating magnetic field using techniques standard in the field of paleomagnetics. This was then added to a 500 ml bottle of the water, shaken vigorously, run through additional cycles of alternating-field demagnetization, and the residual (un-dispersed) particles allowed to settle to the bottom. The supernatant liquid, now 'spiked' with ppb-levels of dispersed magnetite, was then further diluted to a volume of several liters for the balloon freezing experiments.

To quantify the amount of ferromagnetic material in the water samples (pure, spiked, and tap), a class 1000 clean-lab facilities at the California Institute of Technology Paleomagnetics and Biomagnetics laboratories was used. The standard techniques for assessing the ferromagnetic particles within various type of water were modified to carry out the measurements, with sensitivity limits down to the pico-gram/gram range. All sample manipulations and experiments were done in the HEPA-filtered air in the laboratory, including the sample access chamber of the superconducting moment magnetometer. All glassware was soaked in concentrated HCl to solubilize and remove ferromagnetic contaminants. Approximately 8 g of each liquid was transferred into custom quartz-glass cups, into the center of which we positioned the tip of a ~20 cm long, 3 mm quartz-glass NMR tube. To prevent magnetic particles from physically rotating relative to each other (and hence reducing their net magnetic moment gained after exposure to external magnetic fields), the cup assemblies were then positioned on a cryogenic plate and allowed to freeze solid. Prior to measurement on the superconducting moment magnetometers, the glass was removed by gentle warming, leaving the ~8 g of ice frozen on the end of the glass holder. A complete series of rock-magnetic analyses were then performed at sub-freezing temperatures in a HEPA-filtered nitrogen atmosphere within the superconducting moment magnetometers. In particular, coercivity spectra were measured via the acquisition and alternating-field (Af) demagnetization of the isothermal remnant magnetism (IRM), and inter-grain interaction effects were measured using acquisition of anhysteretic remanent magnetism (ARM), as well as on the blank quartz-glass holder for assessing signal to noise. Measured concentrations, based on saturation magnetic remanence values (half that of the full saturation values) are reported in Table 2.

The experiments described herein were designed to test the effect of nanophase magnetite in the magnetite/maghemite solid solution series on both the volume change during freezing, and the degree of supercooling, as compared with control samples of purified water. These are actually separate questions, which can be analyzed independently. Nine trials of both groups were run, as shown in Table 1. The quantitative measure of volume change was computed as a percentage, taken directly from before and after freezing as mentioned above. For the supercooling there were two obvious, and easily-quantified parameters: (1) the time taken from when the balloon first crossed the freezing point (0° C.) until the temperature spike from crystallization appeared, and (2) the lowest temperature reached before that spike (These are shown schematically in FIG. 1, panel a). The null hypothesis of no effect is tested easily with Students' t-test of means for unpaired samples with unequal variance (heteroscedastic), using two-tailed tests. The independence of the volumetric and thermal analyses, and the overall simplicity, argues that a more complex ANOVA is not needed. Statistical comparisons with the tap water samples were not performed, as the materials in it are uncharacterized (except for the magnetization); results are shown here for the sake of qualitative comparison.

Table 1 and FIG. 1 show results from the freezing experiments. The transition from supercooled to the partially frozen state was easily discerned by the abrupt rise in temperature due to the latent heat of crystallization of ice, which quickly brought the entire sphere up to the freezing point.

Table 2 shows results from the superconducting magnetometry done to assess the background levels of ferromagnetic materials present in the samples. Magnetization levels of frozen cubes of the purified water samples are only slightly above background noise of the instrument system using the acid-washed quartz glass holder, whereas the purified water with the addition of magnetite, as well as the tap water, both had easily detectable levels of ferromagnetic particles. The concentration of magnetite in the 'spiked' water used in our freezing experiments was about 70 ppb, whereas the tap water was about 2 ppb. However, magnetic interaction data indicate that the ferromagnetic particles in the tap water are more finely dispersed than those in the magnetite-spiked ultrapure water.

All experiments with purified water run in the polyurethane balloons exhibited clear and obvious supercooling, taking an average of about two hours after crossing the freezing point to reach temperatures between about −11 and −13° C.; this is illustrated in FIG. 1 panel a. In contrast, the purified water to which tiny concentrations of nanophase magnetite crystals had been added displayed far less supercooling, with average temperatures reaching only about −3° C. Both the measured time, and the minimum temperature reached, before the onset of freezing were shorter, or higher, in comparison with the purified water samples (both P-values are <<0.0001). Hence, it is possible to state with very high confidence that nanophase magnetite comparable to that found in many biological tissues provide effective ice crystal nucleation sites.

Table 1 also shows results of four trials ran with the tap water. These results are remarkably consistent in terms of their lack of supercooling, with very short time intervals between reaching 0° C. and the onset of the stable freezing regime.

Figure 3:
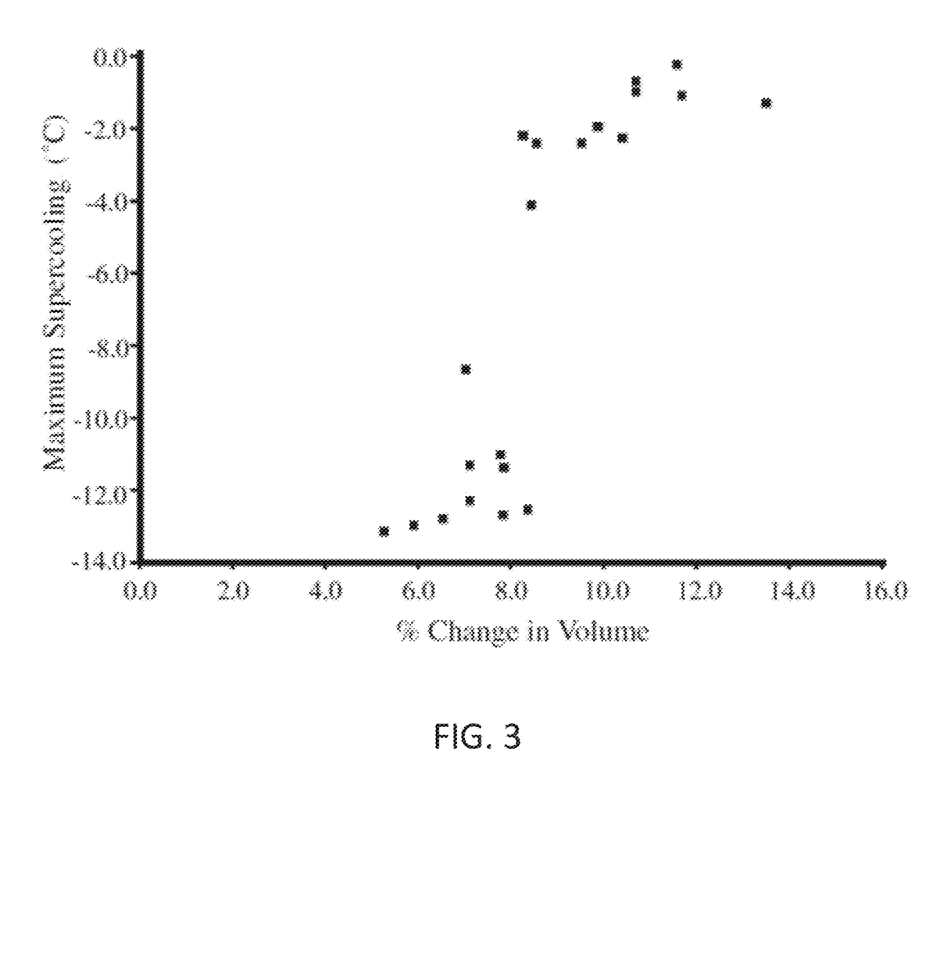
FIG. 3 illustrates a relationship between the measured volume change in the standardized polyurethane balloons and the minimum supercooling temperature.

Surprisingly, it was also found that the balloons with purified water did not expand as much upon freezing as did those that were spiked with magnetite, or even the tap water; these data are shown in Table 1 and FIG. 3. The measured volumetric changes were between about 6 and 8% for the supercooled group, compared with 7-13% for the magnetite-spiked group; this difference is highly significant at the $P<0.01$ level as shown in Table 1. Qualitatively, it can be noticed that supercooled, pure-water balloons maintained more spherical shapes than those that did not supercool.

FIG. 3 illustrates a relationship between the measured volume change in the standardized polyurethane balloons and the minimum supercooling temperature reached in each experiment (data from Table 1). It can be noted that all visible bubbles were removed from the water samples when the balloons were filled, but that any air bubbles formed during the freezing process will contribute to the measured values.

Results shown here clearly support the hypothesis that nanocrystals of magnetite act as effective ice crystal nucleation particles. This is the first experimental test of this effect with this mineral, which is one of the most widely-dispersed mineral products in the biosphere, as well as being common trace mineral in the natural environment. Nucleation temperatures that were observed in the presence of magnetite are high in comparison with other cryopreservation systems, which typically supercool to much colder temperatures. A surprising association was also observed between the degree of supercooling and an apparent volume change, which may have implications for cryobiology and cryopreservation.

The observation that the balloon volume varies sharply for those that supercooled to <−4° C. (shown in FIG. 3) was unexpected, and surprising. The balloons that supercooled also displayed fewer elongate ice crystals deforming their shape. Upon closer examination, it seems that ice formed without supercooling may be degassing more, as the impression was that small bubbles were found more often within those balloons than for those that had supercooled; and the presence of bubbles within the balloons would obviously have a significant effect on the volume measurement. It might be that supercooling to <−4° C. promotes the entrapment of dissolved gasses in a clathrate-like form, and might also promote the formation of the structurally-disordered ice polymorph ($I_{sd}$), instead of the usual hexagonal form ($I_h$), as argued by Malkin et al. in Ref [32]. However, Malkin did not comment on volumetric differences between the two ice states (disordered $I_{sd}$, and ordered $I_h$). Nevertheless, a decrease in degassing within a biological cell during freezing would similarly decrease the net volume change, and potentially result in less damage to biological membranes.

The experiments described herein were designed to mimic the freezing process of typical biological tissues, which for the human food supply are on the order of a few hundred grams or more in size. However, it is worth comparing the results to kindred experiments that have been done in the atmospheric sciences trying to understand the chemistry and kinetics of heterogeneous ice nucleating particles in supercooled water droplets suspended at high altitudes in clouds. In particular, Atkinson et al. in Ref. [1] and Whale et al. in Ref. [49] describe experiments on arrays of hundreds of microliter-sized water droplets, spiked with suspensions of powdered minerals at concentrations up to 1%, held on hydrophobic slides and imaged during the cooling process. Atkinson and Whale concluded that the potassium feldspars minerals were most effective of all of the common dust minerals they examined in the heterogeneous nucleation of ice in supercooled droplets (although Atkinson and Whale did not test magnetite). (It can be noted that nanophase magnetite also commonly exsolves in silicates, and might confound freezing experiments with other minerals). In contrast, the 'drops' described herein were ~140 cc balloons, spiked with ~70 ng/g of standard magnetite powder designed to mimic levels in biological tissues. Due to the much finer grain size or our magnetite, the samples of the present disclosure contain roughly the same active surface area per experiment as did the studies of Atkinson and Whale (within an order of magnitude), and the technique described herein allows easy measurement of volume changes. Comparing the fraction of balloons frozen as temperature falls, to the micro-drop data in FIG. 1 panel a of Atkinson et al. gives a dramatic comparison: the average temperature of magnetite-spiked freezing is about -3° C., compared with -22° C. for solutions of up to 1% K-feldspar. Unfortunately, it is not clear that the microdrop experiments would work well on dense dispersions of magnetite nanoparticles, as the tiny crystals will stick together and drop out of suspension. Nevertheless, it seems that magnetite nucleates ice more efficiently than K-feldspar.

Magnetite nano-crystalline powders, if properly dispersed, might also serve as a simple and effective ice-nucleating agent in a variety of freezing process in which supercooling needs to be avoided. Cochet and Widehem (Ref. [5]) review several of these in the context of using the bacterium, Pseudomonas syringae, to enhance the procedures. These include the preparation of frozen food (wherein supercooling increases the energy cost of freezing), freeze-concentration processes, and spray-ice technology (e.g., snow-making). However, in food application processes the use of magnetite would not require the containment or sterilization processes that are required when using biologically active cells.

Two factors have been discussed extensively in the cryobiology literature, that together seem to influence the viability of tissues and cells during cryopreservation. These include the intracellular formation of ice crystals that can damage and rupture cell membranes, and the change in osmotic and concentration gradients acting between the inside and exteriors of cells during freezing. These factors account for the peak survivability of many tissue types at intermediate cooling rates, and as well as differential revival abilities during subsequent warming stages. However, reasons for the success of various cryopreservation techniques in some organisms, and their dismal failure in related species (e.g., monkeys vs. humans) have been mystifying. It can be noted that biological magnetite concentrations are also highly variable between tissue types within a given species, and between many animal groups. In addition, magnetite is often present as environmental contaminants at variable trace levels in many growth media used to main cell lines in culture. Coupled with the observation reported here that magnetite is an effective ice-crystal nucleating material, it may help resolve some of this variability in cryopreservation. New analytical techniques such as scanning SQUID microscopy and quantum-diamond magnetic imaging are capable of detecting single crystals of biological magnetite within cells, and could potentially test this hypothesis.

It can further be noted that magnetite is a ferromagnetic (more specifically, ferrimagnetic) material. The apparent action of weak, ~10 Hz, ~1 mT oscillating magnetic fields to minimize ice crystal damage in plant and animal tissues during freezing might be explained simply by the induced, magneto-mechanical motion of these nanoparticles of magnetite disturbing incipient nucleation sites on the magnetite crystal surfaces, promoting local supercooling. This hypothesis side-steps many of the biophysical critiques that have been leveled against the "Cells Alive System". In terms of cryobiology, the experiments described herein indicate that the trace amounts of magnetite that are present in many biological tissues ought to nucleate at least some fraction of the ice crystals that cause tissue damage during freezing. Two observations suggest that the sudden crystallization of such supercooled water might minimize cellular damage, including the lower volumetric expansion noted in FIG. 3, and the tendency of supercooled water to generate the structurally-disordered ice polymorph ($I_{sd}$), which does not form needle-like crystals like the more slowly-grown hexagonal ice, $I_h$. As noted above, a single 50 nm particle of magnetite suspended in a 50 mm cell would occupy a volume fraction of 1 ppb; many animal and plant tissues have finely-distributed magnetite crystals at levels that are well above this. It is intriguing that externally-oscillating magnetic fields acting on magnetite crystals might allow the nucleating process to be switched on or off during the freezing process, allowing greater control of the resulting ice crystal size and morphology. Further experimental tests of this hypothesis are in progress.

Therefore, magnetite/maghemite particles, for example dispersed in a liquid solution, may be employed in many different applications, to control freezing. For example, the magnetite particles may be used to prevent excessive supercooling by acting as nucleation sites for ice. Supercooling, or excessive supercooling, may be a negative feature in certain applications. For example, in frozen food supercooling increases the energy cost of freezing. Magnetite particles could be used to aid freezing of food by greatly reducing supercooling. Similar applications of magnetite may be in freeze-concentration processes, and spray-ice technology (e.g., snow-making). For example, magnetite particles in a water solution may be sprayed on a slope to create snow. The magnetite particles may also be injected in a cloud for producing rain.

In some embodiments, a solution containing magnetite particles could be sprayed on fruit, such as citrus fruit, in agriculture applications. The magnetite particles would act as nucleation sites, preventing excessive supercooling of water, and aiding in the formation of ice in ambient temperatures that risk freezing of the citrus fruit. The latent heat of crystallization of the water on the surface (80 calories/gram) as it freezes will buffer the temperature of the interior of the fruit, thereby delaying the formation of damaging ice on the inside; supercooled water would not release this heat, so the addition of nanophase magnetite to prevent supercooling would be beneficial. Generally speaking, fruit and other food can be termed as edible matter, or more generally as biological tissue.

In other embodiments, an oscillating magnetic field can be applied to the magnetite particles during freezing. The magnetic field can be turned on and off to control the ice nucleation. In fact, when the field is on the ice nucleation is inhibited by the oscillation of the magnetic particles, which prevents nucleation and promotes supercooling. When the field is off, the ice nucleation is promoted by the magnetic particles, and supercooling is reduced. By controlling the applied magnetic field, it is therefore possible to control ice nucleation and supercooling. In this way, it is possible to control the ice crystal size and morphology. For example, needle shaped ice crystals may be inhibited or promoted. The change in volume of the liquid upon freezing may also be controlled in a similar way.

Dispersion of the magnetite nanoparticles in liquid can be achieved either physically by grinding and mixing in an inert material, or with other techniques such as inducing magnetite crystal formation from solution, then diluting that solution to the appropriate levels. It could also be done by mixing dry magnetite nanoparticles in a material like a salt, then melting it at temperatures above the Curie temperature of magnetite (~580° C.) so the magnetostatic attraction between nanocrystals goes away, and then mixing and cooling the salt with the dispersed particles trapped. Dissolving small quantities of the magnetite-spiked salt in water would then provide an effective method of producing the concentrations needed for effective control of ice crystal nucleation.

In some embodiments, the magnetite solution may be applied onto or inserted into biological tissues or fluids, such as embryos to be frozen, or tissues or fluids to be frozen. In some embodiments, a magnetite particles solution can be used for controlling heat input and output within a system. For example, a high speed train may travel within a long-distance vacuum tunnel between cities. In vacuum, it may be important to control heat caused by the train's travelling within the tunnel. If a freezing-based temperature control system is used to control heat, the temperature control system may advantageously employ a magnetite solution.

As understood by the person of ordinary skill in the art, a large number of minerals exist. The present disclosure describes how magnetite is superior to other materials in controlling ice nucleation and supercooling. This discovery allows for several commercial and industrial application to be developed.

TABLE 1

| Date of Expt. | Volume | | | SuperCooling Data | |
|---|---|---|---|---|---|
| | Before (ml) | After (ml) | Change (%) | Freezing Time (hr) | SuperCool Temp (° C.) |
| Purified Water Trials: | | | | | |
| May 1, 2015 | 140 | 150 | 7.1 | 2.21 | −12.30 |
| May 12, 2015 | 140 | 150 | 7.1 | 1.57 | −11.30 |
| May 14, 2015 | 141 | 152 | 7.8 | 1.58 | −11.00 |
| May 19, 2015 | 140 | 151 | 7.9 | 1.35 | −11.36 |
| May 21, 2015 | 155 | 168 | 8.4 | 2.21 | −12.55 |
| May 26, 2015 | 153 | 163 | 6.5 | 3.17 | −12.80 |
| May 28, 2015 | 153 | 162 | 5.9 | 2.42 | −12.70 |
| Jun. 29, 2015 | 152 | 161 | 5.9 | 1.94 | −12.99 |
| Jul. 3, 2015 | 152 | 160 | 5.3 | 2.77 | −13.16 |
| N = 9 | Mean: | | 6.9 | 2.14 | −12.24 |
| | S.D.: | | 1.1 | 0.60 | 0.81 |
| Purified Water + Magnetite Trials: | | | | | |
| Apr. 30, 2015 | 133 | 144 | 8.3 | 0.28 | −2.20 |
| May 11, 2015 | 140 | 152 | 8.6 | 0.15 | −2.40 |
| May 13, 2015 | 142 | 152 | 7.0 | 0.13 | −4.10 |
| Jul. 2, 2015 | 142 | 152 | 7.0 | 0.57 | −8.65 |
| Jul. 6, 2015 | 162 | 178 | 9.9 | 0.71 | −1.96 |
| Jul. 8, 2015 | 147 | 161 | 9.5 | 1.03 | −2.41 |
| Jul. 9, 2015 | 148 | 168 | 13.5 | 0.23 | −1.30 |
| Jul. 16, 2015 | 154 | 172 | 11.7 | 0.65 | −1.10 |
| Jul. 18, 2015 | 144 | 159 | 10.4 | 0.68 | −2.26 |
| N = 9 | Mean: | | 9.5 | 0.49 | −2.93 |
| | S.D.: | | 2.1 | 0.31 | 2.31 |
| Tap Water Trials (not used in statistics): | | | | | |
| May 16, 2015 | 140 | 155 | 10.7 | 0.14 | −0.70 |
| May 18, 2015 | 140 | 155 | 10.7 | 0.17 | −1.00 |
| Jun. 17, 2015 | 131 | 152 | 16.0 | 0.06 | −0.20 |
| Jul. 1, 2015 | 138 | 154 | 11.6 | 0.06 | −0.23 |
| N = 4 | Mean: | | 12.3 | 0.11 | −0.53 |
| | S.D.: | | 2.5 | 0.06 | 0.39 | t-tests of means: Purified Water vs. Magnetite-spiked purified water

| | d.f. | t-value | 2-tailed P-value | Significance |
|---|---|---|---|---|
| Volume difference: | 16 | 3.36 | 5.79E−03 | ** |
| Time to Freezing: | 16 | 7.34 | 9.00E−06 | **** |
| Lowest Supercooling Temp.: | 16 | 11.43 | 4.90E−07 | **** |

TABLE 2

| Sample | Mass (g) | Saturation moment (Am2) | Magnetization (Am2/Kg) | Cisowski's R-value | ARM/IRM Suscept. | M.D.F. for IRM (mT) | SD Magnetite equivalent (ng/g) |
|---|---|---|---|---|---|---|---|
| Purified Water | 8.04 | 9.80E−11 | 1.22E−08 | 0.39 | 0.08 | 39.8 | 0.3 |
| Purified Water + Magnetite | 8.12 | 2.54E−08 | 3.13E−06 | 0.27 | 0.01 | 17.4 | 68.1 |
| Tap water | 7.92 | 7.64E−10 | 9.65E−08 | 0.40 | 0.10 | 37.1 | 2.1 |

As visible in FIG. 2, the refrigerating apparatus comprises Styrofoam™ walls (205), as well as an electric fan (210), and the sample is placed in the center (215).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] J. D. Atkinson, B. J. Murray, M. T. Woodhouse, T. F. Whale, K. J. Baustian, K. S. Carslaw, S. Dobbie, D. O'Sullivan, T. L. Malkin, The importance of feldspar for ice nucleation by mineral dust in mixed-phase clouds, Nature 498 (2013) 355-358.

[2] R. F. Butler, Paleomagnetism: Magnetic Domains to Geologic Terranes, Black-well Scientific Publications, Boston, 1992.

[3] R. F. Butler, S. K. Banerjee, Theoretical single-domain size range in magnetite and titanomagnetite, J. Geophys. Res. 80 (1975) 4049-4058.

[4] S. Cisowski, Interacting vs. non-interacting single-domain behavior in natural and synthetic samples, Phys. Earth Planet. Inter. 26 (1981) 56-62.

[5] N. Cochet, P. Widehem, Ice crystallization by pseudomonas syringae, Appl. Microbiol. Biot. 54 (2000) 153-161.

[6] R. Dahl, L. A. Staehelin, High-pressure freezing for the preservatino of biological structure—theory and practice, J. Electron Microsc. Tech. 13 (1989) 165-174.

[7] J. C. Diaz Ricci, J. L. Kirschvink, Magnetic domain state and coercivity predictions for biogenic greigite (Fe3S4): a comparison of theory with magneto-some observations, J. Geophys. Res. 97 (1992) 17309-17315.

[8] J. Dobson, P. Grass, Magnetic properties of human hippocampal tissue—evaluation of artefact and contamination sources, Brain Res. Bull. 39 (1996) 255-259.

[9] J. R. Dunn, M. Fuller, J. Zoeger, J. Dobson, F. Heller, J. Hammann, E. Caine, B. M. Moskowitz, Magnetic material in the human hippocampus, Brain Res. Bull. 36 (1995) 149-153.

[10] J. M. Feinberg, R. J. Harrison, T. Kasama, R. E. Dunin-Borkowski, G. R. Scott, P. R. Renne, Effects of internal mineral structures on the magnetic remanence of silicate-hosted titanomagnetite inclusions: an electron holography study, J. Geophys. Res. Solid Earth 111 (2006).

[11] J. M. Feinberg, G. R. Scott, P. R. Renne, H. R. Wenk, Exsolved magnetite inclusions in silicates: features determining their remanence behavior, Geology 33 (2005) 513-516.

[12] R. B. Frankel, R. P. Blakemore, R. S. Wolfe, Magnetite in freshwater magneto-tactic bacteria, Science 203 (1979) 1355e1356.

[13] M. Gajdardziska-Josifovska, R. G. McClean, M. A. Schofield, C. V. Sommer, W. F. Kean, Discovery of nanocrystalline botanical magnetite, Eur. J. Mineral. 13 (2001) 863-870.

[14] J. L. Gould, J. L. Kirschvink, K. S. Deffeyes, Bees have magnetic remanence, Science 201 (1978) 1026-1028.

[15] R. A. Holland, J. L. Kirschvink, T. G. Doak, M. Wikelski, Bats use magnetite to detect the Earth's magnetic field, Plos One 3 (2008)-1676-6.

[16] M. Kaku, T. Kawata, S. Abedini, H. Koseki, S. Kojima, H. Sumi, H. Shikata, M. Motokawa, T. Fujita, J. Ohtani, N. Ohwada, M. Kurita, K. Tanne, Electric and magnetic fields in cryopreservation: a response, Cryobiology 64 (2012) 304-305.

[17] J. L. Kirschvink, Rock magnetism linked to human brain magnetite, EOS Trans. Am. Geophys. Union 75 (1994) 178-179.

[18] J. L. Kirschvink, D. S. Jones, B. J. McFadden, Magnetite Biomineralization and Magnetoreception in Organisms: a New Biomagnetism, Plenum Press, New York, N.Y., 1985.

[19] J. L. Kirschvink, A. Kobayashi, B. J. Woodford, Magnetite biomineralization in the human brain, Proc. Natl. Acad. Sci. 89 (1992) 7683-7687.

[20] J. L. Kirschvink, R. E. Kopp, T. D. Raub, C. T. Baumgartner, J. W. Holt, Rapid, precise, and high-sensitivity acquisition of paleomagnetic and rock-magnetic data: development of a low-noise automatic sample changing system for superconducting rock magnetometers, Geochem. Geophys. Geosyst. 9 (2008) 1-18.

[21] J.-L. Kirschvink, H. A. Lowenstam, Mineralization and magnetization of chiton teeth: paleomagnetic, sedimentologic, and biologic implications of organic magnetite, Earth Planet. Sci. Lett. 44 (1979) 193-204.

[22] A. Kobayashi, J. L. Kirschvink, A ferromagnetic model for the action of electric and magnetic fields in cryopreservation, Cryobiology 68 (2014) 163-165.

[23] A. Kobayashi, J. L. Kirschvink, C. Z. Nash, R. E. Kopp, D. A. Sauer, L. E. Bertani, W. F. Voorhout, T. Taguchi, Experimental observation of magnetosome chain collapse in magnetotactic bacteria: sedimentological, paleomagnetic, and evolutionary implications, Earth Planet. Sci. Lett. 245 (2006) 538-550.

[24] A. Kobayashi, J. L. Kirschvink, M. H. Nesson, Ferromagnets and EMFs, Nature 374 (1995), 123-123.

[25] A. Kobayashi, N. Yamamoto, J. L. Kirschvink, Studies of inorganic crystals in biological tissue—magnetite in human tumor, J. Jpn. Soc. Powder Powder Metall. 44 (1997) 294-300.

[26] D. Le Sage, K. Arai, D. R. Glenn, S. J. DeVience, L. M. Pham, L. Rahn-Lee, M. D. Lukin, A. Yacoby, A. Komeili, R. L. Walsworth, Optical magnetic imaging of living cells, Nature 496 (2013), 486-U105.

[27] S. Y. Lee, G. W. Huang, J. N. Shiung, Y. H. Huang, J. H. Jeng, T. F. Kuo, J. C. Yang, W. C. V. Yang, Magnetic cryopreservation for dental pulp stem cells, Cells Tissues Organs 196 (2012) 23-33.

[28] P. Y. Lin, Y. C. Yang, S. H. Hung, S. Y. Lee, M. S. Lee, M. Chu, S. M. Hwang, Cryo-preservation of human embryonic stem cells by a programmed freezer with an oscillating magnetic field, Cryobiology 66 (2013) 256-260.

[29] H. A. Lowenstam, Magnetite in denticle capping in recent chitons (polyplacophora), Geol. Soc. Am. Bull. 73 (1962) 435-438.

[30] H. A. Lowenstam, Minerals made by organisms, Science 211 (1981) 1126-1131.

[31] H. A. Lowenstam, S. Weiner, On Biomineralization, Oxford University Press, Oxford, 1989.

[32] T. L. Malkin, B. J. Murray, C. G. Salzmann, V. Molinero, S. J. Pickering, T. F. Whale, Stacking disorder in ice I, Phys. Chem. Chem. Phys. 17 (2015) 60-76.

[33] S. Mann, N. H. C. Sparks, M. M. Walker, J. L. Kirschvink, Ultrastructure, morphology and organization of biogenic magnetite from sockeye salmon, Oncorhynchus nerka: implications for magnetoreception, J. Exp. Biol. 140 (1988) 35-49.

[34] P. Mazur, S. P. Leibo, G. E. Seidel, Cryopreservation of the germplasm of animals used in biological and medical research: importance, impact, status, and future directions, Biol. Reprod. 78 (2008) 2-12.
[35] E. B. Moore, V. Molinero, Structural transformation in supercooled water controls the crystallization rate of ice, Nature 479 (2011), 506-U226.
[36] G. J. Morris, E. Acton, Controlled ice nucleation in cryopreservation—a review, Cryobiology 66 (2013) 85-92.
[37] U. Munro, J. A. Munro, J. B. Phillips, R. Wiltschko, W. Wiltschko, Evidence for a magnetite-based navigational map in birds, Naturwissenschaften 84 (1997) 26-28.
[38] N. Owada, S. Kurita, in: U.S.p. office (Ed.), Super-quick Freezing Method and Apparatus Therefor, ABI Limited, Chiba, Japan, United States of America, 2001. U.S. Pat. No. 6,250,087 B1.
[39] N. Owada, S. Saito, in: U.S.p. office (Ed.), Quick Freezing Apparatus and Quick Freezing Method, 2010, p. 15. U.S. Pat. No. 7,810,340 B2, Owada, N., United States of America.
[40] D. J. Saville, Multiple comparison procedures—the practical solution, Am. Stat. 44 (1990) 174-180.
[41] R. A. Shaw, A. J. Durant, Y. Mi, Heterogeneous surface crystallization observed in undercooled water, J. Phys. Chem. B 109 (2005) 9865-9868.
[42] T. Suzuki, Y. Takeuchi, K. Masuda, M. Watanabe, R. Shirakashi, Y. Fukuda, T. Tsuruta, K. Yamamoto, N. Koga, N. Hiruma, J. Ichioka, K. Takail, Experimental investigation of effectiveness of magnetic field on food freezing process, Trans. Jpn. Soc. Refrig. Air Cond. Eng. 26 (2009) 371-386.
[43] J. A. Tarduno, R. D. Cottrell, A. V. Smirnov, High geomagnetic intensity during the mid-cretaceous from Thellier analyses of single plagioclase crystals, Science 291 (2001) 1779-1783.
[44] J. A. Tarduno, R. D. Cottrell, M. K. Watkeys, D. Bauch, Geomagnetic field strength 3.2 billion years ago recorded by single silicate crystals, Nature 446 (2007) 657-660.
[45] C. Walcott, J. L. Gould, J. L. Kirschvink, Pigeons have magnets, Science 205 (1979) 1027-1029.
[46] M. M. Walker, J. L. Kirschvink, S.-B. R. Chang, A. E. Dizon, A candidate magnetic sense organ in the Yellowfin Tuna Thunnus albacares, Science 224 (1984) 751-753.
[47] M. M. Walker, J. L. Kirschvink, A. S. Perry, A. E. Dizon, Methods and techniques for the detection, extraction, and characterization of biogenic magnetite, in: J. L. Kirschvink, D. S. Jones, B. J. McFadden (Eds.), Magnetite Biomineralization and Magnetoreception in Organisms: a New Biomagnetism, Plenum Press, New York, 1985, pp. 154-166.
[48] B. P. Weiss, F. J. Baudenbacher, J. P. Wikswo, J. L. Kirschvink, Magnetic microscopy promises a leap in sensitivity and resolution, Eos Trans. AGU 82 (2001) 513-518.
[49] T. F. Whale, B. J. Murray, D. O'Sullivan, T. W. Wilson, N. S. Umo, K. J. Baustian, J. D. Atkinson, D. A. Workneh, G. J. Morris, A technique for quantifying heterogeneous ice nucleation in microliter supercooled water droplets, Atmos. Meas. Tech. 8 (2015) 2437-2447.
[50] W. Wiltschko, U. Munro, R. C. Beason, H. Ford, R. Wiltschko, A magnetic pulse leads to a temporary deflection in the orientation of migratory birds, Experimentia 50 (1994) 697-700.
[51] B. Wowk, Electric and magnetic fields in cryopreservation, Cryobiology 64 (2012) 301-303.
[52] X. X. Zhang, M. Chen, M. Fu, Impact of surface nanostructure on ice nucleation, J. Chem. Phys. 141 (2014).

What is claimed is:

1. A method of cryopreserving edible matter comprising: controlling ice nucleation and supercooling in a liquid solution, the liquid solution comprising magnetite particles, by spraying said liquid solution onto the edible matter, wherein the controlled liquid solution cryopreserves the edible matter.

2. The method of claim 1, wherein controlling ice nucleation and supercooling in the liquid solution comprises promoting ice nucleation and inhibiting supercooling.

3. The method of claim 1, wherein controlling ice nucleation and supercooling in the liquid solution comprises inhibiting ice nucleation and promoting supercooling by applying an oscillating magnetic field to said liquid solution.

4. The method of claim 2, wherein the liquid solution comprises water.

5. The method of claim 1, further comprising freezing the edible matter.

* * * * *